United States Patent [19]

Garritano et al.

[11] Patent Number: 5,520,042
[45] Date of Patent: May 28, 1996

[54] APPARATUS AND METHOD FOR THE SIMULTANEOUS MEASUREMENT OF RHEOLOGICAL AND THERMAL CHARACTERISTICS OF MATERIALS AND MEASURING CELL THEREFOR

[75] Inventors: Ronald F. Garritano, Flemington; Michael Goncharko, Millstone; Mahesh Padmanabhan, Piscataway, all of N.J.

[73] Assignee: Rheometric Scientific, Piscataway, N.J.

[21] Appl. No.: 491,682

[22] Filed: Jun. 19, 1995

[51] Int. Cl.⁶ ................................................. G01N 11/00
[52] U.S. Cl. ........................ 73/54.02; 73/843; 374/46
[58] Field of Search .................... 73/843, 822, 794, 73/53.06, 54.02, 861.02, 861.03, 863.11, 866, 61.42, 61.46, 51.24; 374/33, 34, 40, 41, 46, 48, 204, 110, 112

[56] References Cited

U.S. PATENT DOCUMENTS

| | | |
|---|---|---|
| 3,182,494 | 4/1969 | Beatty et al. .............................. 374/48 |
| 3,488,992 | 1/1970 | Veith et al. ................................ 374/48 |
| 3,513,699 | 5/1970 | Reilly, Jr. . |
| 3,527,923 | 9/1970 | O'Neill . |
| 3,593,577 | 7/1971 | Monner . |
| 3,643,491 | 2/1972 | Dell et al. . |
| 3,667,294 | 6/1972 | Schoenlaub . |
| 3,747,396 | 7/1973 | O'Neill . |
| 3,813,937 | 6/1974 | Fletcher et al. . |
| 4,130,016 | 12/1978 | Walker . |
| 4,166,385 | 9/1979 | Pate et al. . |
| 4,530,608 | 7/1985 | O'Neill . |
| 4,601,195 | 7/1986 | Garritano . |
| 4,848,921 | 7/1989 | Kunze . |
| 5,138,872 | 8/1992 | Henderson .............................. 73/64.41 |
| 5,167,143 | 12/1992 | Brookfield ............................. 73/54.39 |
| 5,224,775 | 7/1993 | Reading et al. . |
| 5,271,675 | 12/1993 | Fagan et al. ............................ 374/110 |

*Primary Examiner*—Richard Chilcot
*Assistant Examiner*—Max Noori
*Attorney, Agent, or Firm*—Samuelson & Jacob

[57] ABSTRACT

Apparatus and method for the simultaneous measurement of rheological and thermal characteristics of a test specimen subjects the test specimen to stress for rheological measurements, while at the same time subjecting the same test specimen to controlled temperature changes for the measurement of temperature differentials indicative of thermal characteristics of the test specimen while the test specimen is being stressed for the rheological measurements, and a measuring cell for measuring the thermal characteristics of a specimen.

43 Claims, 4 Drawing Sheets

COMBINED RHEOLOGICAL AND THERMAL ANALYSIS OF A POLYMER 5,520,042

APPARATUS AND METHOD FOR THE SIMULTANEOUS MEASUREMENT OF RHEOLOGICAL AND THERMAL CHARACTERISTICS OF MATERIALS AND MEASURING CELL THEREFOR

The present invention relates generally to the measurement of rheological and thermal characteristics of materials and pertains, more specifically, to apparatus and method for the simultaneous measurement of these characteristics, as well as to a measuring cell utilized in the apparatus and method.

In the evaluation of various characteristics of materials, several different analytical techniques often are employed in the testing of a particular material, since a single technique seldom yields sufficient information to fully characterize the material. These different techniques usually are performed serially on a single test specimen, or are performed on multiple test specimens, requiring close duplication of testing conditions and environments in order to enable accurate correlation of the results of all of the individual tests. Such close duplication is difficult, at best, and is almost impossible under most circumstances, especially where only limited quantities of a particular material are available for testing, and where time and facilities are limited.

The present invention enables the conduct of simultaneous analytical techniques on a single test specimen, thereby eliminating differences in test results which might otherwise result from variations in sample size, morphology, orientation, or conditioning of test specimens, as well as from variations in testing conditions and environments. More specifically, the present invention enables the simultaneous measurement of rheological characteristics and thermal characteristics of materials heretofore evaluated in separate analytical procedures utilizing separate analytical instruments and provides a measuring cell particularly well-suited to attaining such simultaneous measurements, as well as for measuring thermal characteristics in industrial process environments in addition to laboratory settings.

Accordingly, the present invention attains several objects and advantages, some of which are summarized as follows: Enables the simultaneous performance of different analytical techniques on a single test specimen for rapid and practical characterization of materials with increased accuracy; provides for the simultaneous measurement of rheological and thermal characteristics of materials for the accurate characterization of materials with increased ease and economy; eliminates the need for multiple test procedures and concomitant difficult correlations among the results of such multiple test procedures; eliminates differences in data due to variations in sample size, morphology, orientation, or conditioning of test specimens; provides relatively simple, easily operated apparatus and procedure for accomplishing the measurement of rheological and thermal characteristics of a wide variety of materials; enables the simultaneous measurement of even very dissimilar characteristics for increased flexibility with economy; combines rheological and thermal analysis of materials in a practical and extremely workable manner made available for use in both laboratory and actual manufacturing environments; provides a compact and self-contained measuring cell for measuring thermal characteristics of materials with increased ease, flexibility and reliability in industrial process machinery, as well as in laboratory apparatus; provides a rugged construction suitable for use in connection with industrial process machinery as well as laboratory apparatus; enables ease of maintenance and cleaning, as well as use, in both laboratory and manufacturing settings.

The above objects and advantages, as well as further objects and advantages, are attained by the present invention which may be described briefly as apparatus for the simultaneous measurement of rheological and thermal characteristics of a test specimen, the apparatus comprising: opposed first and second platens spaced apart axially for receiving the test specimen between the platens and coupling the test specimen to the platens; displacement means for displacing one of the first and second platens relative to the other of the first and second platens to stress the test specimen and provide information indicative of rheological characteristics of the test specimen; heat flux means juxtaposed with at least the first platen for changing the temperature of the test specimen; a body of heat conductive material integrated with the first platen and interposed between the heat flux means and the test specimen so as to conduct heat between the heat flux means and the test specimen with a minimum of resistance to the conduct of heat through the body; a first temperature detector for detecting the temperature of the body of heat conductive material; a second temperature detector for detecting the temperature of the test specimen, the second temperature detector being placed at a location adjacent the body of heat conductive material; and thermal resistance means between the body of heat conductive material and the location of the second temperature detector for resisting thermal conductivity between the body of heat conductive material and the second temperature detector, whereby differences in temperature detected by the first temperature detector and the second temperature detector provide information indicative of thermal characteristics of the test specimen while the test specimen is stressed between the first and second platens to provide said information indicative of rheological characteristics of the test specimen.

In addition, the invention includes method for the simultaneous measurement of rheological and thermal characteristics of a test specimen, the method comprising: coupling a test specimen to opposed first and second platens spaced apart axially for receiving the test specimen between the platens; displacing one of the first and second platens relative to the other of the first and second platens to stress the test specimen and provide information indicative of rheological characteristics of the test specimen; changing the temperature of the test specimen by conducting heat between a heat flux means and the test specimen through a body of heat conductive material integrated with the first platen and interposed between the heat flux means and the test specimen so as to conduct heat between the heat flux means and the test specimen with a minimum of resistance to the conduct of heat through the body; detecting the temperature of the body of heat conductive material; detecting the temperature of the test specimen at a location adjacent the body of heat conductive material and relatively thermally isolated from the body of heat conductive material; and providing information indicative of thermal characteristics of the test specimen, based upon differences in temperature detected by the first temperature detector and the second temperature detector, while the test specimen is stressed between the first and second platens to provide said information indicative of rheological characteristics of the test specimen.

Further, the invention includes a measuring cell for use in connection with a heat flux means in the measurement of thermal characteristics of a specimen of material, the measuring cell comprising: a body of heat conductive material for being interposed between the heat flux means and the specimen so as to conduct heat between the heat flux means and the specimen with a minimum of resistance to the conduct of heat through the body; a first temperature detector for detecting the temperature of the body of heat conductive material; a second temperature detector for detecting the temperature of the specimen, the second temperature detector being placed at a location adjacent the body of heat conductive material; and thermal resistance means between the body of heat conductive material and the location of the second temperature detector for resisting thermal conductivity between the body of heat conductive material and the second temperature detector, whereby differences in temperature detected by the first temperature detector and the second temperature detector provide information indicative of thermal characteristics of the specimen.

The invention will be understood more fully, while still further objects and advantages will become apparent, in the following detailed description of preferred embodiments of the invention illustrated in the accompanying drawing, in which.

Figure 1:
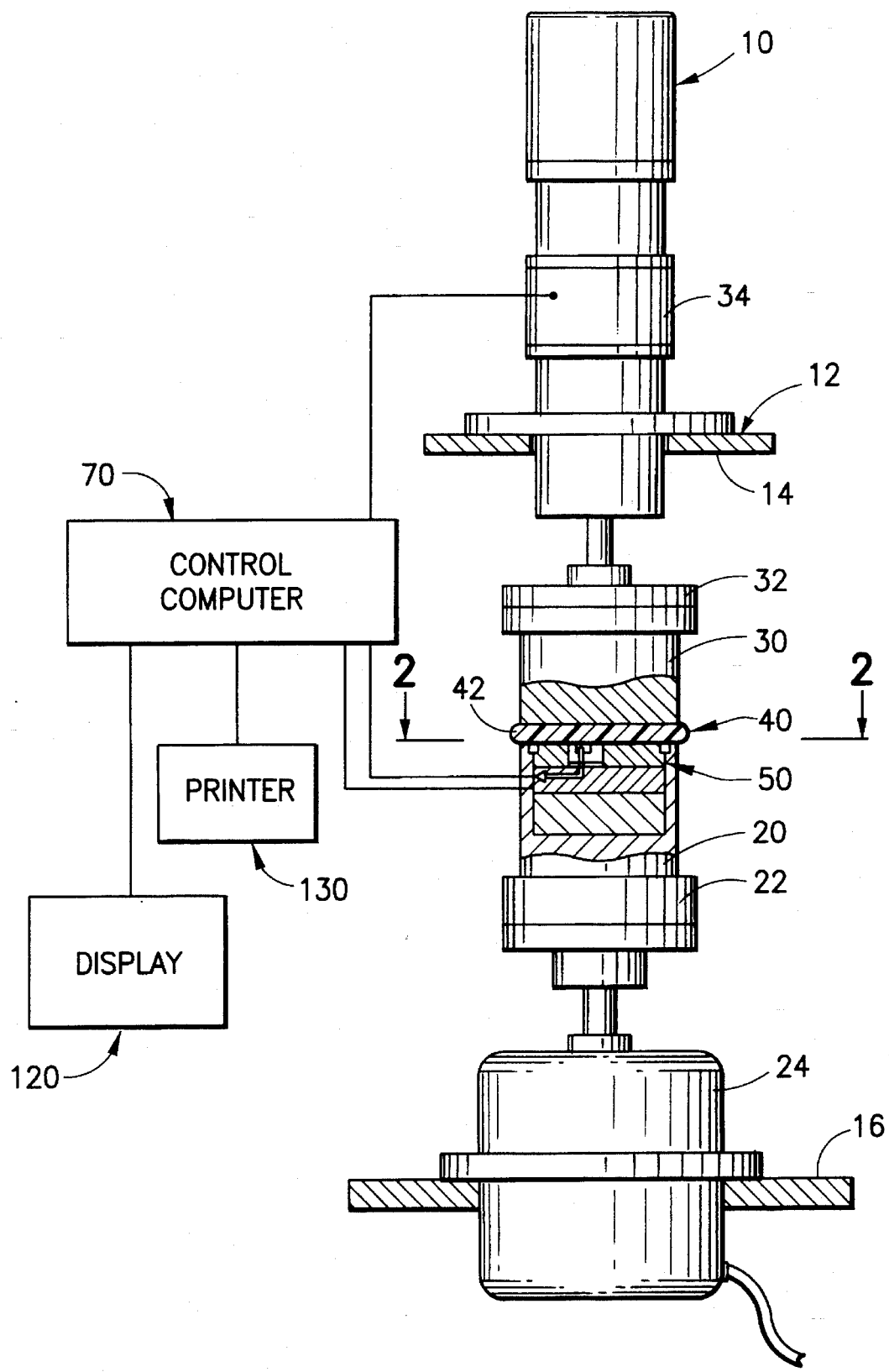
FIG. 1 is an elevational view, partially sectioned and partially diagrammatic, illustrating an apparatus constructed in accordance with the invention.

Referring now to the drawing, and especially to FIG. 1 thereof, an apparatus constructed in accordance with the present invention is illustrated generally at 10 and is seen to include a frame 12 having an upper support member 14 and a lower support member 16. A first, or lower platen 20 is coupled, by means of a lower coupling 22, to a motor 24 mounted upon lower member 16. An opposite second, or upper platen 30, spaced axially from the lower platen 20, is coupled, by means of an upper coupling 32, to a transducer assembly 34 mounted upon upper support member 14.

A test specimen 40 of viscoelastic material is placed between the lower platen 20 and the upper platen 30 and is coupled to both the lower and upper platens 20 and 30. In this instance, the test specimen 40 is in the form of a disk 42 of polymer melt whose viscoelastic properties are to be measured, in a manner now well known in the art of rheometry. One apparatus which illustrates the manner in which rheological characteristics of a test specimen, such as test specimen 40, are to be measured is shown in U.S. Pat. No. 4,601,195, the disclosure of which is incorporated herein by reference thereto.

As set forth above, it is advantageous to be able to conduct different analytical procedures simultaneously, using the same test specimen, to measure different characteristics of the test specimen without requiring multiple serial procedures. Thus, apparatus 10 provides for the measurement of thermal characteristics of test specimen 40 simultaneously with the measurement of rheological characteristics of the same test specimen 40. To that end, apparatus 10 includes a heated and cooled stage 50 in the lower platen 20 arranged to measure the thermal behavior of test specimen 40 at the same time that the test specimen 40 is being stressed to measure rheological behavior.

Figure 2:
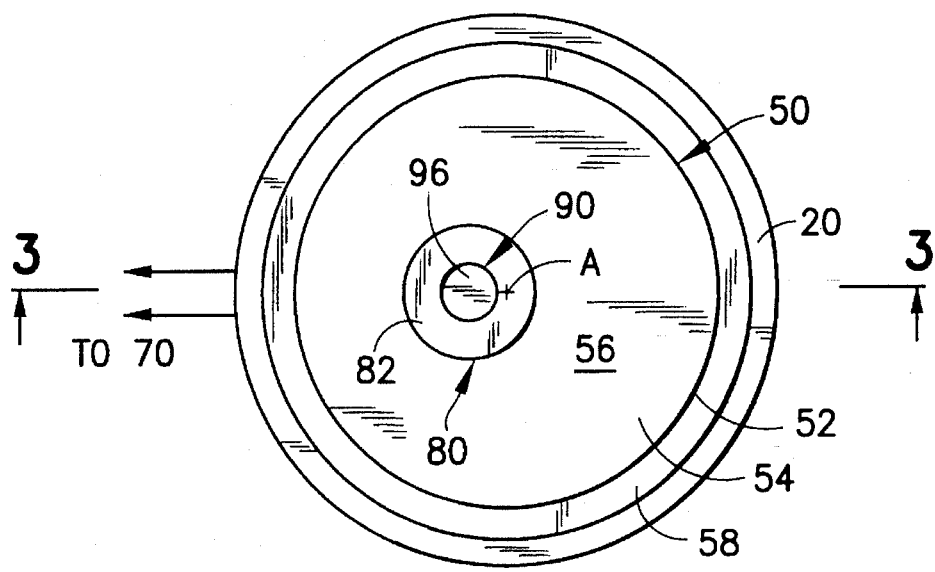
FIG. 2 is an enlarged plan view taken in the direction of the arrows in FIG. 1.
Figure 4:
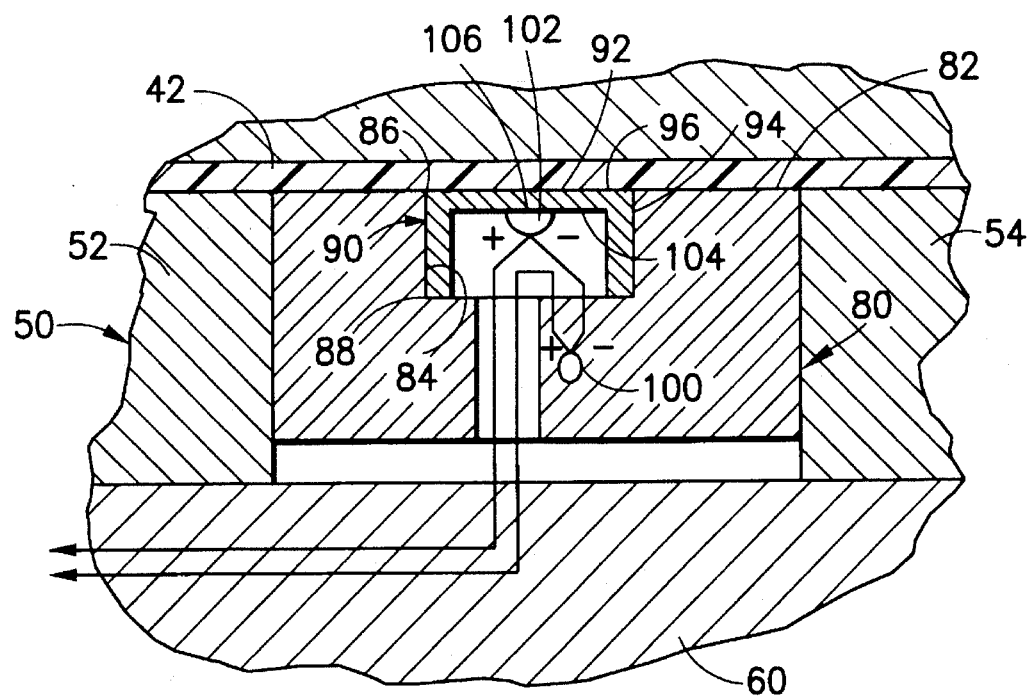
FIG. 4 is a still further enlarged fragmentary cross-sectional view of a portion of FIG. 3.
Figure 3:
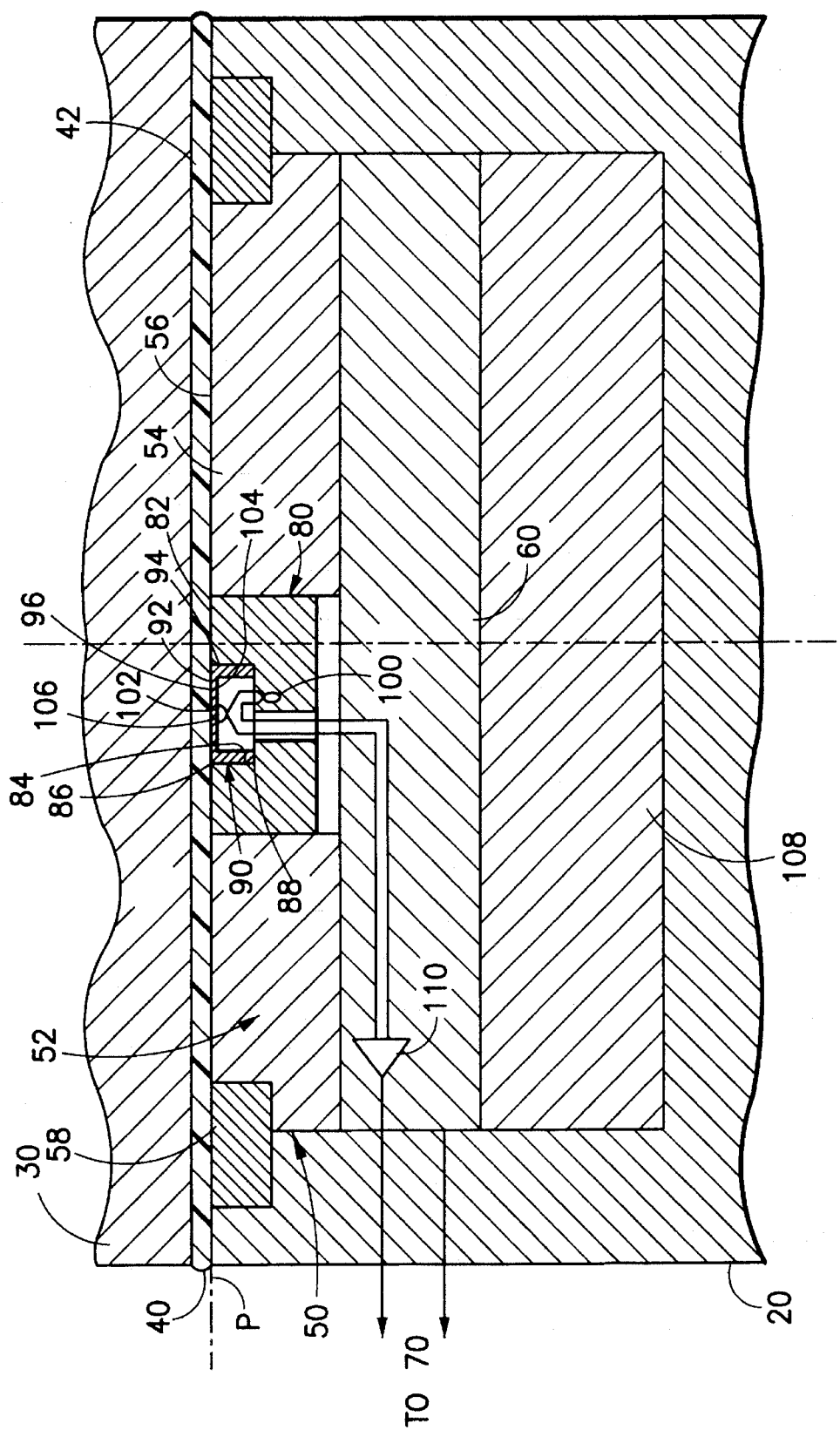
FIG. 3 is a further enlarged fragmentary cross-sectional view taken along line 3—3 of FIG. 2.

Turning now to FIGS. 2 through 4, as well as to FIG. 1, heated stage 50 includes a measuring cell 52 secured within the lower platen 20. Measuring cell 52 has a plate 54 of heat conductive material, such as copper, plate 54 including an upper surface 56 and being affixed within the lower platen 20 by means of a retainer ring 58, which allows selective removal and replacement of the measuring cell 52, as desired. A heat flux means, shown in the form of a peltier element 60, is juxtaposed with the lower platen 20 and is arranged to supply heat to the test specimen 40, and to remove heat from the test specimen 40, as controlled by a control computer 70 (see FIG. 1). A body of highly heat conductive and relatively inert material, such as silver, is shown in the form of a stabilizer block 80 secured within plate 54 so as to be integrated with the plate 54, as will be described more fully below. Stabilizer block 80 has an upper surface 82, and a well 84 extends axially into the stabilizer block 80, from a top end 86 at the upper surface 82, to a bottom end 88, and is closed by a member in the form of a cap 90 having a cup-like configuration including a disk-like top wall 92 and a unitary sleeve-like side wall 94 depending from the top wall 92. The preferred material for cap 90 is stainless steel. The cap 90 is telescoped into the well 84 and is secured in place by the fit between the side wall 94 and the well 84, with upper surface 96 of the top wall 92 flush with upper surface 82 of the stabilizer block 80, which upper surface 82 is, in turn, flush with the upper surface 56 of the plate 54; that is, upper surfaces 56, 82 and 96 all extend within a common radial plane P. At the same time, upper surface 82 is fully contiguous with upper surface 56, which surrounds upper surface 82 in radial directions, and upper surface 96 is fully contiguous with upper surface 82, which surrounds upper surface 96 in radial directions. In this manner, the test specimen 40 is maintained fully against the upper surfaces 56, 82 and 96, in intimate contact with the upper surfaces 56, 82 and 96, while the test specimen 40 is fully coupled to the lower platen 20. Further, the flush configuration establishes a rugged construction capable of withstanding conditions encountered in both laboratory use and use in connection with process measurements in production machines, while enabling ease of cleaning and maintenance in both laboratory and industrial environments.

A first temperature detector is shown in the form of a thermocouple 100 embedded within the body of the stabilizer block 80, while a second temperature detector is shown in the form of a thermocouple 102 secured to the cap 90, at the inner surface 104 of the top wall 92 of the cap 90 and preferably centered within top end 86 of the well 84. Thus, the cap 90 and the well 84, by virtue of the material of the cap 90, which is a relatively poor conductor of heat, compared to the heat conductivity of the material of stabilizer block 80, and the location of the cap 90 in the well 84, serve as thermal resistance means placed between the material of stabilizer block 80 and a location 106, which location 106 thus is adjacent the stabilizer block 80 and somewhat thermally isolated from the stabilizer block 80 so as to resist thermal conductivity between the stabilizer block 80 and the location 106. The thermocouple 102 is placed at location 106 and consequently is somewhat isolated thermally from stabilizer block 80; that is, the thermal resistance means provided by the well 84 and the cap 90 resists thermal conductivity between the stabilizer block 80 and the thermocouple 102. The rate at which heat is supplied from the peltier element 60 to the test specimen 40, or is removed by the peltier element 60 from the test specimen 40, is controlled by the control computer 70, and a heat sink 108 assists in the operation of the peltier element 60. Thermocouples 100 and 102 are connected in such manner as to provide an indication of differences in temperature detected by the thermocouples 100 and 102, and an amplifier 110 is responsive to the differences in temperature detected by the thermocouples 100 and 102 for transmitting corresponding signals to the control computer 70.

In order to measure both rheological characteristics and thermal characteristics of the test specimen 40 simultaneously, the test specimen 40 is coupled to the lower and upper platens 20 and 30, and the lower and upper platens 20 and 30 are displaced relative to one another to stress the test specimen 40. The transducer assembly 34 then provides a signal to the control computer 70 indicative of the rheological characteristics to be measured. The relative displacement is accomplished by rotation of the lower platen 20 relative to the upper platen 30 about an axis of rotation A, and the test specimen 40 is subjected to shear stress, in a now well known manner. At the same time, heat is supplied to the test specimen 40, or is conducted from the test specimen 40, at a controlled rate, by the peltier element 60 and the control computer 70, and the amplifier 108 provides a signal to the control computer 70 indicative of the thermal characteristics to be measured.

The rather large mass of the highly heat conductive material of stabilizer block 80, and the larger area of upper surface 82 of the stabilizer block 80, as compared to the mass of the relatively thin, cup-shaped member of less heat conductive material of cap 90 and the lesser area of upper surface 96, and the hollow nature of the well 84, all enable the thermocouple 100 to detect the temperature of the test specimen 40 as that temperature is changed upwardly and downwardly, either through linear up and down profiles or through sinusoidal profiles, or combinations of such profiles, by the operation of the peltier element 60 and the control computer 70, with the thermocouple 100 following a more-or-less evened-out overall temperature of the test specimen 40, by virtue of the relatively low thermal resistance between the test specimen 40 and the stabilizing block 80, while thermocouple 102, which is relatively isolated thermally from the highly heat conductive material of the stabilizer block 80 by virtue of the relatively high thermal resistance established by the well 84 and the cap 90, as described above, detects differences in temperature of the test specimen 40 between the location 106, in the vicinity of the thermocouple 102, and the stabilizer block 80, which differences arise as a result of changes in thermal properties, such as those changes resulting from specific heat, heat of fusion and heat of crystallization, occurring in the material of the test specimen 40 at certain temperatures. In this manner, temperature differentials arising from changes occurring in the test specimen 40 itself, while heat is conducted to or from the test specimen 40, are measured by the differences in temperature detected at the thermocouples 100 and 102. It is noted that the location of thermocouple 102 in the illustrated embodiment is offset laterally from the axis of rotation A, that is, thermocouple 102 is spaced laterally away from the axis of rotation A, so that the thermocouple 102 is located at a position where the test specimen 40 is stressed, thereby enabling the evaluation of the effect of shear stress upon the thermal properties being measured, one such thermal property being shear-induced crystallization.

Figure 5:
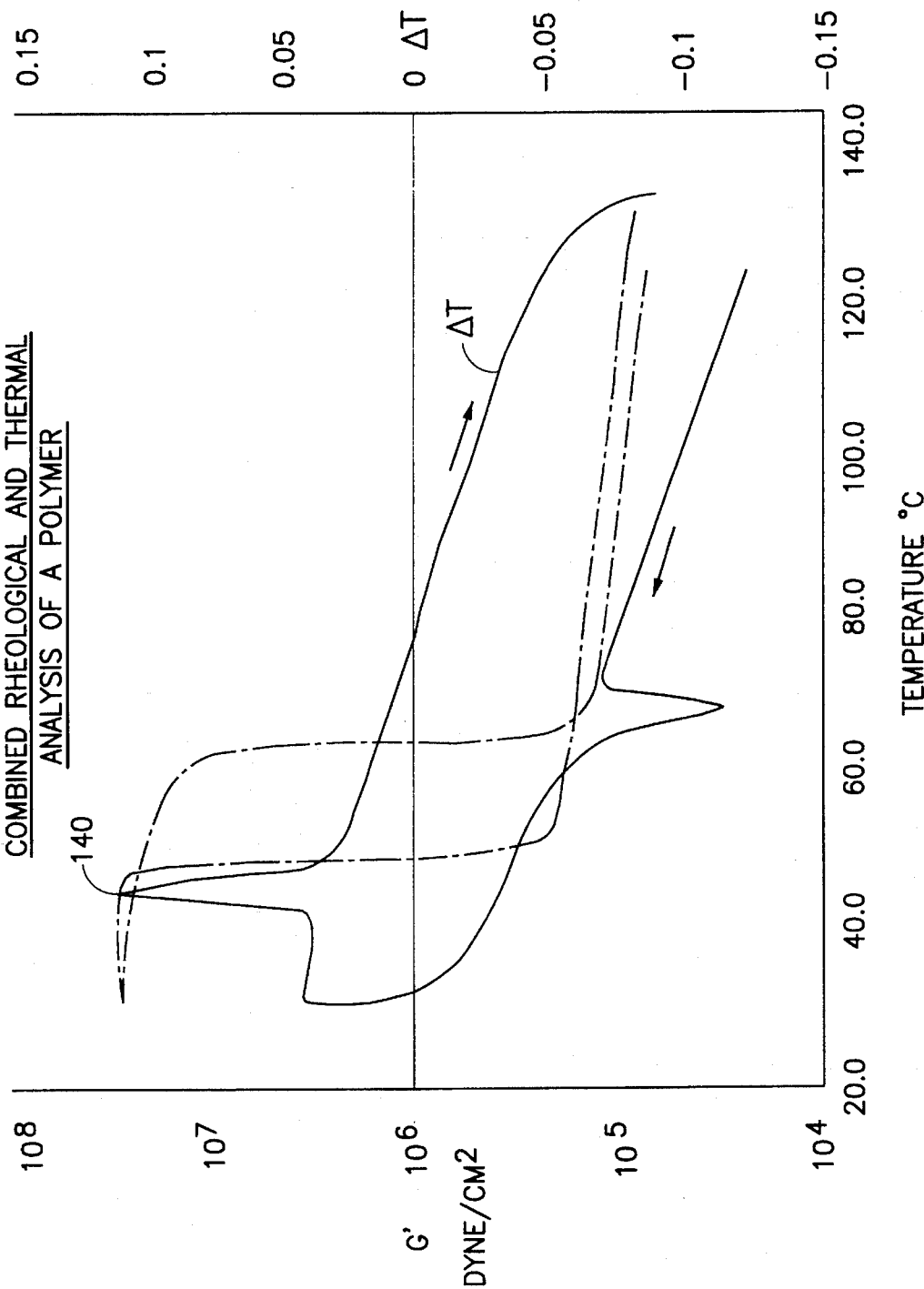
FIG. 5 is a diagram illustrating typical data obtained in the practice of the invention.

The rheological characteristics and the thermal characteristics are displayed at a visual display 120 and are printed at a printer 130. Data obtained from a test specimen 40 of a typical polymer melt is illustrated in FIG. 5 wherein both shear modulus (G') and differential temperature measurements ($\Delta T$), measured simultaneously as described above, are plotted against temperature over a range of changing temperature, providing a direct correlation between thermal transitions and rheological behavior of the test specimen. As the material is cooled, the material crystallizes, as illustrated by the exothermic peak at 140, and the shear modulus rises rapidly, as seen at 142, due to the change to a solid state. During heating, the shear modulus falls again, as seen at 144, as the material melts, as shown by the endothermic peak at 146. This direct correlation is attained quickly and with a high degree of accuracy by the simultaneous measurements enabled by the apparatus and procedure of the present invention.

It will be seen then, that the present invention attains the several objects and advantages summarized above; namely: Enables the simultaneous performance of different analytical techniques on a single test specimen for rapid and practical characterization of materials with increased accuracy; provides for the simultaneous measurement of rheological and thermal characteristics of materials for the accurate characterization of materials with increased ease and economy; eliminates the need for multiple test procedures and concomitant difficult correlations among the results of such multiple test procedures; eliminates differences in data due to variations in sample size, morphology, orientation, or conditioning of test specimens; provides relatively simple, easily operated apparatus and procedure for accomplishing the measurement of rheological and thermal characteristics of a wide variety of materials; enables the simultaneous measurement of even very dissimilar characteristics for increased flexibility with economy; combines rheological and thermal analysis of materials in a practical and extremely workable manner made available for use in both laboratory and actual manufacturing environments; provides a compact and self-contained measuring cell for measuring thermal characteristics of materials with increased ease, flexibility and reliability in industrial process machinery, as well as in laboratory apparatus; provides a rugged construction suitable for use in connection with industrial process machinery as well as laboratory apparatus; enables ease of maintenance and cleaning, as well as use, in both laboratory and manufacturing settings.

It is to be understood that the above detailed description of preferred embodiments of the invention is provided by way of example only. Various details of design, construction and procedure may be modified without departing from the true spirit and scope of the invention, as set forth in the appended claims.

The embodiments of the invention in which an exclusive property or privilege is claimed are defined as follows:

1. Apparatus for the simultaneous measurement of rheological and thermal characteristics of a test specimen, the apparatus comprising:

opposed first and second platens spaced apart axially for receiving the test specimen between the platens and coupling the test specimen to the platens;

displacement means for displacing one of the first and second platens relative to the other of the first and second platens to stress the test specimen and provide information indicative of rheological characteristics of the test specimen;

heat flux means juxtaposed with at least the first platen for changing the temperature of the test specimen;

a body of heat conductive material integrated with the first platen and interposed between the heat flux means and the test specimen so as to conduct heat between the heat flux means and the test specimen with a minimum of resistance to the conduct of heat through the body;

a first temperature detector for detecting the temperature of the body of heat conductive material;

a second temperature detector for detecting the temperature of the test specimen, the second temperature detector being placed at a location adjacent the body of heat conductive material; and thermal resistance means between the body of heat conductive material and the location of the second temperature detector for resisting thermal conductivity between the body of heat conductive material and the second temperature detector, whereby differences in temperature detected by the first temperature detector and the second temperature detector provide information indicative of thermal characteristics of the test specimen while the test specimen is stressed between the first and second platens to provide said information indicative of theological characteristics of the test specimen.

2. The invention of claim 1 wherein:

the first platen includes a first surface for engaging the test specimen coupled to the first platen;

the body of heat conductive material includes a second surface alongside the first surface for engaging the test specimen coupled to the first platen;

the thermal resistance means include a well extending axially into the body, the well having a top surrounded laterally by the second surface, and a bottom spaced axially from the top;

the first temperature detector is located within the body of heat conductive material, outside the well; and the second temperature detector is located within the well, spaced laterally from the second surface and placed axially at the top of the well for close juxtaposition with the test specimen coupled to the first platen and relative thermal isolation from the body of heat conductive material.

3. The invention of claim 2 wherein the location of the second temperature detector is centered laterally within the well.

4. The invention of claim 1 wherein:

the displacement means rotates one of the first and second platens relative to the other of the first and second platens about an axis of rotation for angular displacement between the first and second platens to stress the test specimen; and the second temperature detector is spaced laterally away from the axis of rotation.

5. The invention of claim 4 wherein:

the first platen includes a first radial surface for engaging the test specimen coupled to the first platen;

the body of heat conductive material includes a second radial surface contiguous with the first radial surface for engaging the test specimen coupled to the first platen;

the thermal resistance means include a well extending axially into the body, the well having a top surrounded laterally by the second radial surface, and a bottom spaced axially from the top;

the first temperature detector is embedded within the body of heat conductive material, outside the well; and the second temperature detector is located within the well, spaced laterally from the second radial surface and placed axially at the top of the well for close juxtaposition with the test specimen coupled to the first platen and relative thermal isolation from the body of heat conductive material.

6. The invention of claim 5 wherein the thermal resistance means include a cap at the top of the well, the cap closing the well and including a third radial surface contiguous with the second radial surface, the second temperature detector being located on the cap, within the well.

7. The invention of claim 6 wherein the first surface, the second surface and the third surface extend within a common plane.

8. The invention of claim 7 wherein the cap comprises a cup-like member telescoped into the well.

9. The invention of claim 7 wherein the location of the second temperature detector is centered radially within the well.

10. The invention of claim 5 wherein the heat conductive material of the body is silver.

11. The invention of claim 10 including a cap at the top of the well, the cap closing the well and including a third radial surface contiguous with the second radial surface, the second temperature detector being located on the cap, within the well.

12. The invention of claim 11 wherein the cap comprises a cup-like member constructed of stainless steel and telescoped into the well.

13. The invention of claim 12 wherein the location of the second temperature detector is centered radially on the cap.

14. Apparatus for the simultaneous measurement of rheological and thermal characteristics of a test specimen, the apparatus comprising:

opposed first and second platens spaced apart axially for receiving the test specimen between the platens and coupling the test specimen to the platens;

displacement means for displacing one of the first and second platens relative to the other of the first and second platens to stress the test specimen and provide information indicative of rheological characteristics of the test specimen;

heat flux means juxtaposed with at least the first platen for changing the temperature of the test specimen;

a stabilizer block of heat conductive material secured within the first platen and interposed between the heat flux means and the test specimen so as to conduct heat between the heat flux means and the test specimen with a minimum of resistance to the conduct of heat through the stabilizer block;

a first temperature detector in the heat conductive material of the stabilizer block for detecting the temperature of the stabilizer block;

a second temperature detector placed at a location adjacent the stabilizer block for detecting the temperature of the test specimen; and thermal resistance means between the heat conductive material of the stabilizer block and the location of the second temperature detector for resisting thermal conductivity between the heat conductive material of the stabilizer block and the second temperature detector, whereby differences in temperature detected by the first temperature detector and the second temperature detector provide information indicative of thermal characteristics of the test specimen while the test specimen is stressed between the first and second platens to provide said information indicative of rheological characteristics of the test specimen.

15. The invention of claim 14 wherein:

the first platen includes an essentially planar first surface for engaging the test specimen coupled to the first platen;

the stabilizer block includes an essentially planar second surface contiguous with the first surface for engaging the test specimen coupled to the first platen;

the thermal resistance means include a well extending axially into the stabilizer block, the well having a top end surrounded laterally by the second surface, and a bottom end spaced axially from the top end;

the first temperature detector is located within the heat conductive material of the stabilizer block, outside the well; and the second temperature detector is located within the well, spaced laterally from the second surface and placed axially at the top end of the well for close juxtaposition with the test specimen coupled to the first platen and relative thermal isolation from the heat conductive material of the stabilizer block.

16. The invention of claim 14 wherein:

the displacement means rotates one of the first and second platens relative to the other of the first and second platens about an axis of rotation for angular displacement between the first and second platens to stress the test specimen; and the second temperature detector is spaced laterally away from the axis of rotation.

17. The invention of claim 16 wherein:

the first platen includes an essentially planar first radial surface for engaging the test specimen coupled to the first platen;

the stabilizer block includes an essentially planar second radial surface contiguous with the first radial surface for engaging the test specimen coupled to the first platen;

the thermal resistance means include a well extending axially into the stabilizer block, the well having a top end surrounded laterally by the second radial surface, and a bottom end spaced axially from the top end;

the first temperature detector is embedded within the heat conductive material of the stabilizer block, outside the well; and the second temperature detector is located within the well, spaced laterally from the second radial surface and placed axially at the top end of the well for close juxtaposition with the test specimen coupled to the first platen and relative isolation from the heat conductive material of the stabilizer block.

18. The invention of claim 17 including a cap at the top end of the well, the cap closing the well and including a third radial surface contiguous with the second radial surface, the second temperature detector being located on the cap, within the well.

19. The invention of claim 18 wherein the first surface, the second surface and the third surface extend within a common plane.

20. The invention of claim 19 wherein the cap comprises a cup-like member telescoped into the well.

21. The invention of claim 19 wherein the location of the second temperature detector is centered radially within the well.

22. The invention of claim 17 wherein the heat conductive material of the stabilizer block is silver.

23. The invention of claim 22 including a cap at the top end of the well, the cap closing the well and including a third radial surface contiguous with the second radial surface, the second temperature detector being located on the cap, within the well.

24. The invention of claim 23 wherein the cap comprises a cup-like member constructed of stainless steel and telescoped into the well.

25. The invention of claim 14 wherein the heat flux means comprises a peltier element.

26. Method for the simultaneous measurement of rheological and thermal characteristics of a test specimen, the method comprising:

coupling a test specimen to opposed first and second platens spaced apart axially for receiving the test specimen between the platens;

displacing one of the first and second platens relative to the other of the first and second platens to stress the test specimen and provide information indicative of rheological characteristics of the test specimen;

changing the temperature of the test specimen by conducting heat between a heat flux means and the test specimen through a body of heat conductive material integrated with the first platen and interposed between the heat flux means and the test specimen so as to conduct heat between the heat flux means and the test specimen with a minimum of resistance to the conduct of heat through the body;

detecting the temperature of the body of heat conductive material;

detecting the temperature of the test specimen at a location adjacent the body of heat conductive material and relatively thermally isolated from the body of heat conductive material; and providing information indicative of thermal characteristics of the test specimen, based upon differences in temperature detected by the first temperature detector and the second temperature detector, while the test specimen is stressed between the first and second platens to provide said information indicative of rheological characteristics of the test specimen.

27. The invention of claim 26 including:

displacing one of the first and second platens relative to the other of the first and second platens by rotating one of the first and second platens relative to the other of the first and second platens about an axis of rotation for angular displacement between the first and second platens to stress the test specimen; and detecting the temperature of the test specimen at the location relatively thermally isolated from the body of heat conductive material, the location being spaced laterally away from the axis of rotation.

28. The invention of claim 27 including detecting the temperature of the body of heat conductive material at a location within the body of heat conductive material while detecting the temperature of the test specimen at the location relatively thermally isolated from the body of heat conductive material.

29. A measuring cell for use in connection with a heat flux means in the measurement of thermal characteristics of a specimen of material, the measuring cell comprising:

a body of heat conductive material for being interposed between the heat flux means and the specimen so as to conduct heat between the heat flux means and the specimen with a minimum of resistance to the conduct of heat through the body;

a first temperature detector for detecting the temperature of the body of heat conductive material;

a second temperature detector for detecting the temperature of the specimen, the second temperature detector being placed at a location adjacent the body of heat conductive material; and thermal resistance means between the body of heat conductive material and the location of the second temperature detector for resisting thermal conductivity between the body of heat conductive material and the second temperature detector, whereby differences in temperature detected by the first temperature detector and the second temperature detector provide information indicative of thermal characteristics of the specimen.

30. The invention of claim 29 wherein:

the body of heat conductive material includes a first surface for engaging the specimen;

the thermal resistance means include a well extending axially into the body, the well having a top surrounded laterally by the first surface, and a bottom spaced axially from the top;

the first temperature detector is located within the body of heat conductive material, outside the well; and the second temperature detector is located within the well, spaced laterally from the first surface and placed axially at the top of the well for close juxtaposition with the specimen and relative thermal isolation from the body of heat conductive material.

31. The invention of claim 30 wherein the location of the second temperature detector is centered laterally within the well.

32. The invention of claim 30 wherein the thermal resistance means include a cap at the top of the well, the cap closing the well and including a second surface contiguous with the first surface, the second temperature detector being located on the cap, within the well.

33. The invention of claim 32 wherein the cap comprises a cup-like member telescoped into the well.

34. The invention of claim 33 wherein the cap is constructed of stainless steel.

35. The invention of claim 29 wherein the heat conductive material of the body is silver.

36. A measuring cell for use in connection with a heat flux means in the measurement of thermal characteristics of a specimen, the measuring cell comprising:

a stabilizer block of heat conductive material interposed between the heat flux means and the specimen so as to conduct heat between the heat flux means and the specimen with a minimum of resistance to the conduct of heat through the stabilizer block;

a first temperature detector in the heat conductive material of the stabilizer block for detecting the temperature of the stabilizer block;

a second temperature detector placed at a location adjacent the stabilizer block for detecting the temperature of the specimen; and thermal resistance means between the heat conductive material of the stabilizer block and the location of the second temperature detector for resisting thermal conductivity between the heat conductive material of the stabilizer block and the second temperature detector, whereby differences in temperature detected by the first temperature detector and the second temperature detector provide information indicative of thermal characteristics of the specimen while the test specimen.

37. The invention of claim 36 wherein:

the stabilizer block includes an essentially planar first surface specimen;

the thermal resistance means include a well extending axially into the stabilizer block, the well having a top end surrounded laterally by the first surface, and a bottom end spaced axially from the top end;

the first temperature detector is located within the heat conductive material of the stabilizer block, outside the well; and the second temperature detector is located within the well, spaced laterally from the first surface and placed axially at the top end of the well for close juxtaposition with the specimen and relative thermal isolation from the heat conductive material of the stabilizer block.

38. The invention of claim 37 wherein the location of the second temperature detector is centered laterally within the well.

39. The invention of claim 37 including a cap at the top end of the well, the cap closing the well and including a second surface contiguous with the first surface, the second temperature detector being located on the cap, within the well.

40. The invention of claim 39 wherein the first surface and the second surface extend within a common plane.

41. The invention of claim 40 wherein the cap comprises a cup-like member telescoped into the well.

42. The invention of claim 41 wherein the cap comprises a cup-like member constructed of stainless steel and telescoped into the well.

43. The invention of claim 36 wherein the heat conductive material of the stabilizer block is silver.

* * * * *